United States Patent [19]

Burns

[11] Patent Number: 5,361,921
[45] Date of Patent: Nov. 8, 1994

[54] COMBINATION STOPPER-SHIELD CLOSURE

[75] Inventor: James A. Burns, Elizabeth, N.J.

[73] Assignee: Becton Dickinson and Company, Franklin Lakes, N.J.

[21] Appl. No.: 84,382

[22] Filed: Jun. 29, 1993

[51] Int. Cl.5 .............................................. B65D 41/28
[52] U.S. Cl. .................... 215/320; 215/247; 215/364
[58] Field of Search ............... 215/364, 358, 355, 320, 215/247, 296, DIG. 3

[56] References Cited

U.S. PATENT DOCUMENTS

| | | | |
|---|---|---|---|
| 4,205,754 | 6/1980 | Nielsen et al. | 215/364 |
| 4,366,912 | 1/1983 | Matukura et al. | 215/364 |
| 4,741,446 | 5/1988 | Miller | 215/247 |
| 4,928,934 | 5/1990 | Morton, Jr. | 206/560 |
| 4,967,919 | 11/1990 | Earhart | 215/247 |
| 5,232,111 | 8/1993 | Burns | 215/320 |

FOREIGN PATENT DOCUMENTS

0419490B1 10/1993 European Pat. Off. .

Primary Examiner—Joseph Man-Fu Moy
Attorney, Agent, or Firm—Alan W. Fiedler

[57] ABSTRACT

A combination stopper and shield closure for sealing the open end of an evacuated body fluid collection tube. The stopper is headless and includes a well in its top surface with an undercut at its base. The shield includes a plurality of flexible fingers extending from its top surface, each finger including a cleat at its proximal end for engaging with the undercut in the stopper. The interaction between the cleats and the undercut serve to securely hold the stopper within the shield and eliminate compression forces being applied to the stopper by the shield. In addition, the base of the well is convex to direct any residue body fluid away from the center of the well towards the undercut and minimize residue build-up, and the bottom portion of the stopper is concave to reduce the thickness of the stopper's diaphragm and reduce penetration force.

8 Claims, 4 Drawing Sheets

COMBINATION STOPPER-SHIELD CLOSURE

BACKGROUND OF THE INVENTION

1. Field of the Invention

The present invention relates to a combination stopper and shield closure for body fluid collection tubes and, more particularly, relates to a closure for an evacuated body fluid collection tube having a headless stopper that minimizes needle penetration force by reducing radial compression interference in the stopper.

2. Background Description

An evacuated body fluid collection tube is commonly used by a doctor, phlebotomist or nurse to draw a sample of body fluid from a patient in a hospital or doctor's office for diagnostic testing. During the use of such a tube, a double-ended needle in a needle holder is inserted in a vein of the patient and the evacuated tube is inserted into the open end of the holder until the needle in the holder pierces the tube's closure. The vacuum in the tube then draws a body fluid sample from the patient into the tube. When draw is completed the tube is removed from the holder and replaced by additional tubes or the holder and tube are removed from the patient's vein. When the body fluid sample in the tube is to be tested, the test sample can either be removed from the tube by removing the closure from the open end of the tube or using a syringe to pierce the closure and draw the test sample from the tube. These alternative methods of removing the test sample from the tube, however, present divergent problems. If the closure is removed from the open end of the tube, it is important that the stopper remain attached to the shield. To avoid this problem it is common to increase the compression forces on the stopper to firmly hold the stopper in the shield. However, if a syringe is used to remove the test sample by piercing the closure it is imperative that the compression forces on the stopper be minimized, since compression of the stopper increases the force needed to pierce the stopper.

Moreover, when using either method it is important for the closure to fit securely on the open end of the tube and maintain the vacuum in the tube before, during and after the collection procedure. The vacuum in the tube must be sufficient to draw body fluid into the tube, since body fluid must be drawn as quickly as possible to minimize the amount of time a patient has one end of the needle in their body, which can be uncomfortable and cause pain. For example, if the vacuum in the tube is deficient, subsequent removal of the tube from the needle holder and insertion of another tube in the needle holder would be necessary which prolongs the unpleasant procedure.

Current closures for evacuated body fluid collection tubes include a plastic shield containing a rubber stopper having an enlarged head portion and a plug portion extending from the bottom of the head portion to be received within and seal the open end of the tube. The stopper in such closures is commonly held within the shield by compression forces on the head of the stopper. An example of this type of closure is described in U.S. Pat. No. 4,967,919 (Earhart).

Those skilled in the art should therefore appreciate the trade-off problems that exist when designing a closure for evacuated body fluid collection tubes between (1) the penetration force necessary for inserting a needle through the closure and (2) the forces needed to withdraw the closure frown the tube and retain the stopper within the shield. Using plastic shields over rubber stoppers provides a firm gripping surface to help the user remove the closure from the evacuated tube and overcome the force of the vacuum within the tube. However, the need for retaining the stopper within the shield during removal has resulted in increased radial compression on the stopper from the shield, which detrimentally increases needle penetration force.

SUMMARY OF THE INVENTION

The present invention overcomes the problems identified in the background material by providing a closure having a shield and a headless stopper, wherein the headless stopper is under minimal radial compression from the shield. The minimized radial compression results in a minimization of needle penetration force through the diaphragm of the stopper without degrading vacuum retention or increasing the force necessary to remove the closure from the tube for testing purposes.

A preferred embodiment of a closure according to the present invention includes a shield and a headless stopper, wherein the shield has a plurality of flexible fingers extending from its top with cleats that engage an undercut at the base of a well in the stopper. Interaction between the cleats and the undercut serve to securely hold the stopper within the shield and minimize compression forces being applied to the stopper by the shield. The well diameter of the stopper is less than the diameter of the flexible fingers of the shield; therefore, when assembled the cleats of the fingers produce a compressive force on the well's undercut resulting in some of the needle penetration area of the stopper being in tension and the remainder being in minimal compression. Likewise, the compressive forces between the cleats and undercut do not detrimentally affect the forces needed to pull the closure out of the open end of the tube. In addition, the base of the well is convex to direct any residue body fluid away from the center of the well towards the undercut and minimize residue build-up, the bottom of the stopper is concave to reduce the thickness of the stopper's diaphragm, and a plurality of sealing rings are located around the circumference of the stopper to provide a vacuum tight seal within an open end of the evacuated tube.

An alternative embodiment of a closure according to the present invention includes an annular groove on the top surface of the stopper located between a central well and the outer circumference of the stopper. The groove having an undercut for receiving cleats at the end of each of a plurality of flexible fingers to retain the stopper within the shield. Alternatively, each flexible finger can have a spur that mates with the wall of the groove.

These and other aspects, features and advantages of the present invention will become apparent from the following detailed description taken in conjunction with the accompanying drawings.

DETAILED DESCRIPTION

Figure 1:
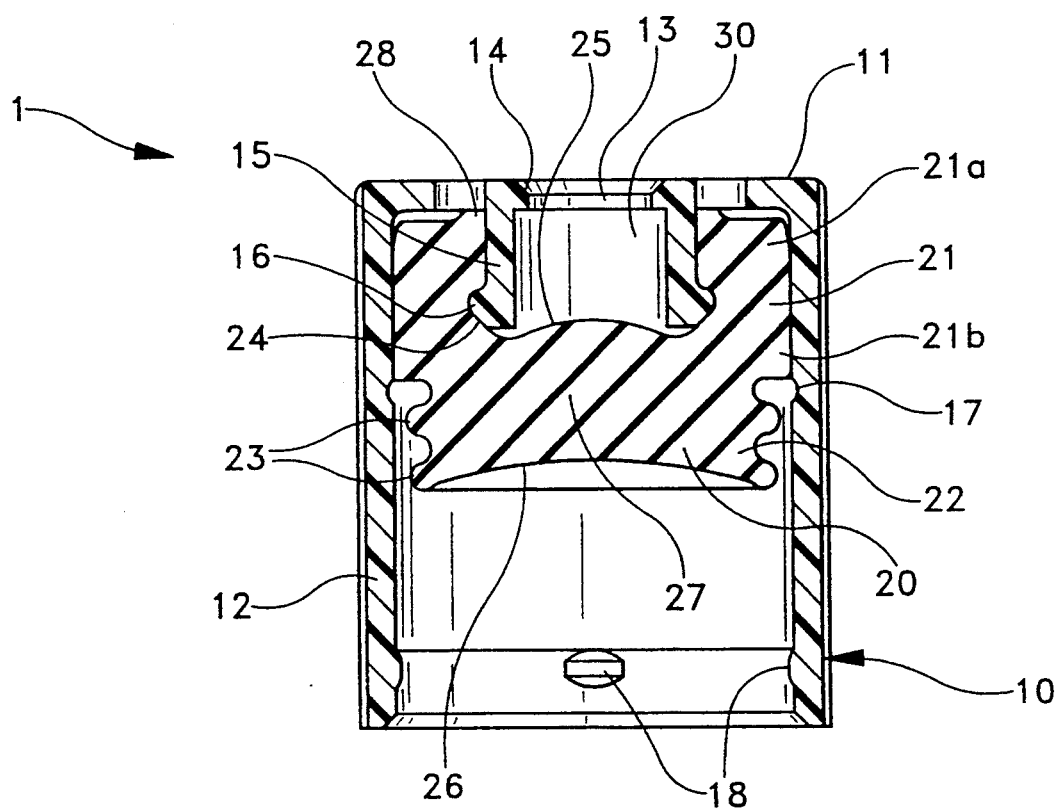
FIG. 1 is a cross-sectional view of a closure according to the present invention taken along lines A—A in FIG. 2.

FIG. 1 is a cross-sectional view of a closure 1 according to the present invention for sealing the open end of an evacuated body fluid collection robe (not shown). Closure 1 includes a shield portion 10 and a stopper portion 20, with stopper 20 having an upper flange 21 having a top section 21a and a lower section 21b and a plug 22 extending from flange 21 to seal the open end of the tube. Flange 21 includes an annular well 30 in its top having an undercut 24 around its convex base 25. The distance between the top of well 30 and base 25 is such that a user cannot come into contact with and contaminate base 25. Plug 22 includes a concave bottom portion 26 to minimize the thickness of a diaphragm 27 and a pair of sealing rings 23 that surround the circumference of plug 22 to provide a vacuum tight seal with an inner wall of the tube when plug 22 is in the open end of the tube.

As shown in FIG. 1, shield 10 includes an outer skirt 12 extending from a top surface 11 that surrounds and encloses stopper 20 to prevent a user from making contact with and contaminating stopper 20. Top surface 11 includes an opening 13 that is deemed by an angled rim 14 to provide access to base 25 in well 30 so that a needle can be inserted through opening 13 and into diaphragm 27 at base 25. Angled rim 14 has a smaller diameter than well 30 to form an edge to trap residue body fluid within well 30 after use. A plurality of flexible fingers 15 extend from the periphery of opening 13, with each finger 15 having a cleat 16 extending from its proximal end away from opening 13 and engaging undercut 24 in base 25, with the diameter of flexible fingers 15 being greater than the diameter of well 30. It must be appreciated. therefore, that primarily the top section 21a of upper flange 21 of stopper 20 in closure 1 is under compression force from fingers 15 since stopper 20 is only held within shield 10 by the springforce between cleats 16 and undercut 24. Therefore, the compressive forces between the fingers and undercut do not detrimentally affect the compression forces in lower section 21b and plug 22 or the forces needed to pull closure 1 out of the open end of the tube.

FIG. 1 also shows a sealing ring 28 surrounding the top of fingers 15 that provides a seal between stopper 20 and shield 10 to prevent body fluid from flowing up fingers 15 and out the top of shield 10. Shield 10 also includes a channel 17 on the inside of skirt 12 and a plurality of protrusions 18 around the bottom of skirt 12 that aid in sealing and snap-locking closure 1 to the evacuated tube. Channel 17 receives and locks with a rim (not shown) around the open end of the tube and/or protrusions 18 lock to a collar or lock ting (not shown) around the outer circumference of the tube.

Figure 2:
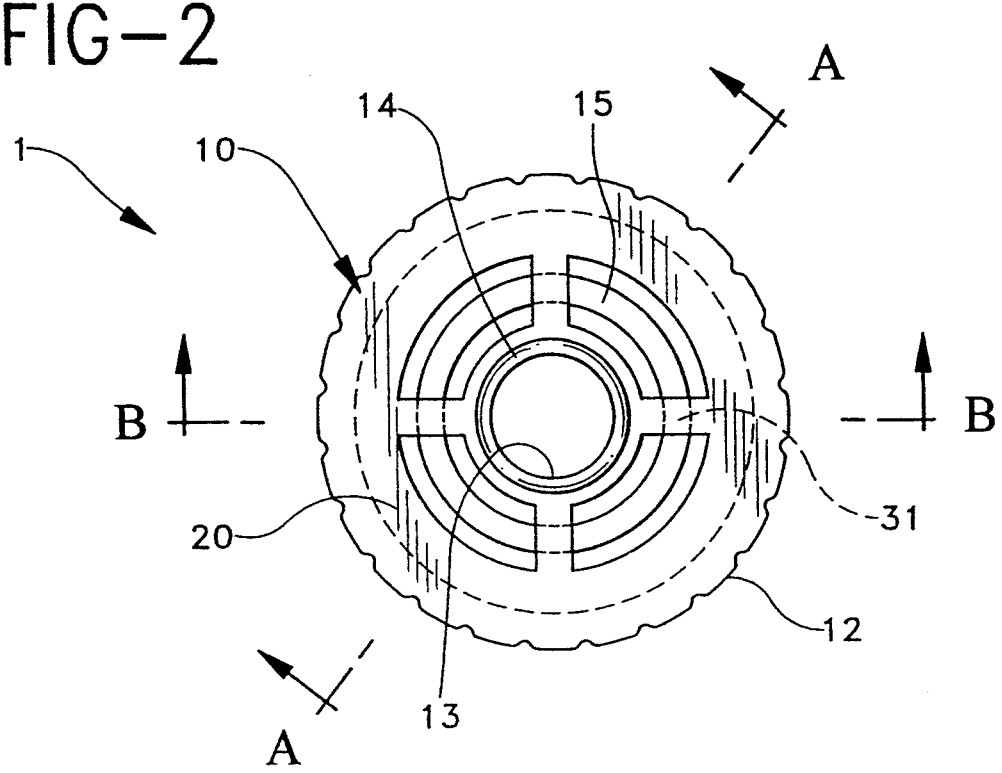
FIG. 2 is a top view of the closure shown in FIG. 1.
Figure 3:
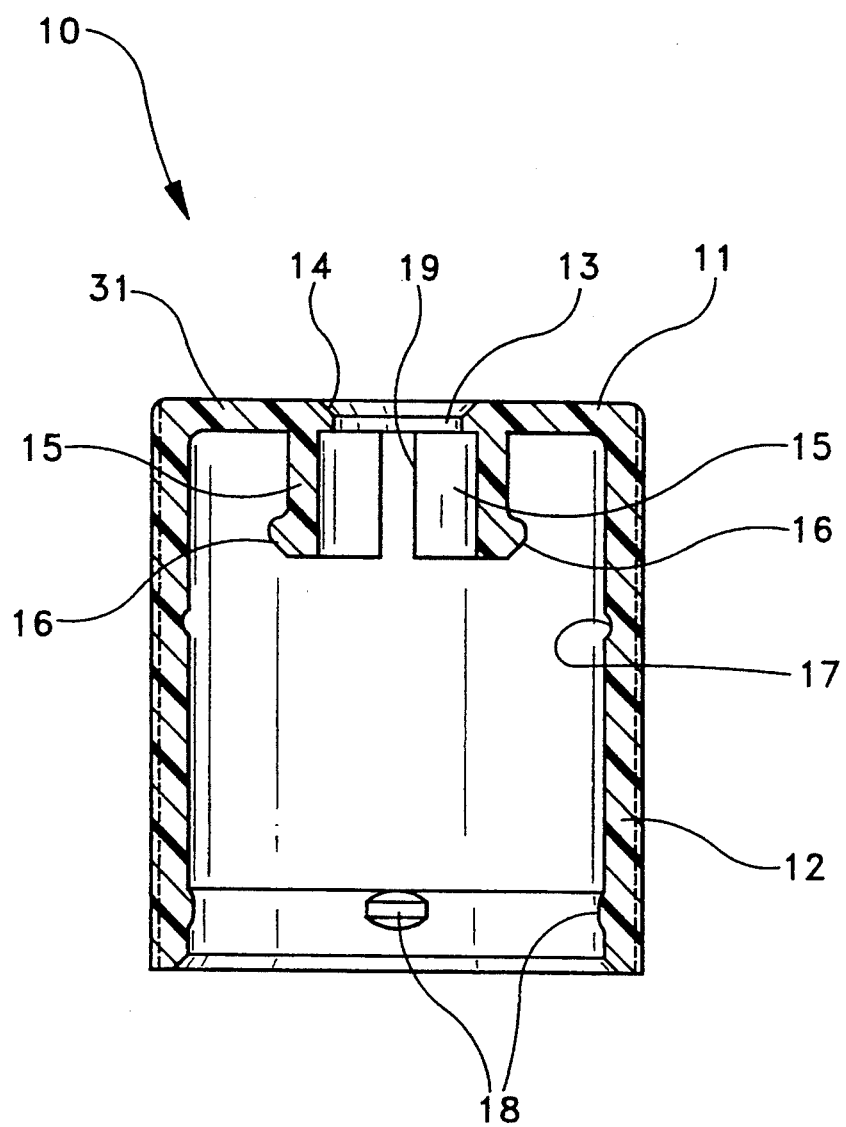
FIG. 3 is a cross-sectional view of the shield shown in FIGS. 1 and 2 taken along lines B—B in FIG. 2.

As shown in more detail in FIGS. 2 and 3, top surface 11 of shield 10 includes a plurality of spokes 31 that support each of the fingers 15 and angled rim 14 of opening 13. In addition, FIG. 2 shows skirt 12 of shield 10 having a ribbed outer surface which provides improved gripping action when the user is rotating and removing closure 1 from the tube in the laboratory. Finally, FIG. 2 shows where the cross-sectional view in FIG. 1 of closure I was taken along lines A—A and where the cross-sectional view in FIG. 3 of shield 10 was taken along lines B—B. FIG. 3 also shows one of a plurality of spaces 19 that separate each of the plurality of flexible fingers 15.

FIGS. 4 through 7 are cross-sectional views of various alternative embodiments of closures that include additional features of the present invention.

Figure 4:
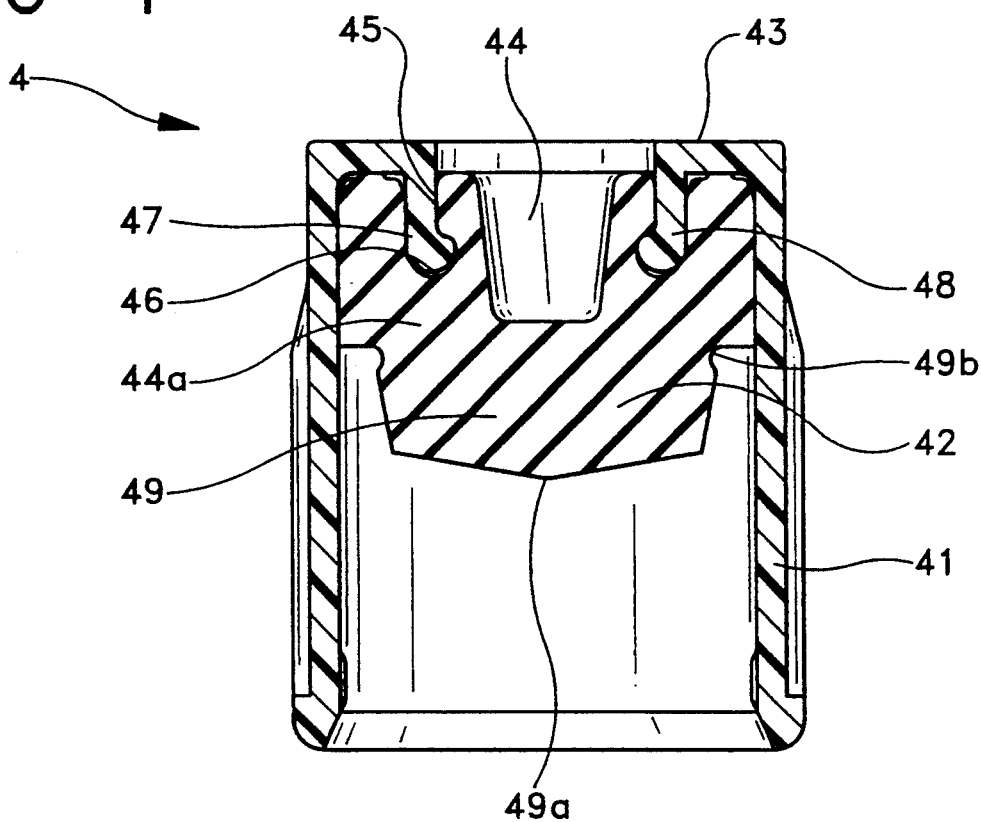
FIGS. 4 through 7 are cross-sectional views of alternative embodiments of closures according to the present invention.

FIG. 4 is a cross-sectional view of an alternative embodiment of a closure 4 according to the present invention that is similar to closure 1 shown in FIGS. 1 through 3. Closure 4 includes a shield 41 for receiving a stopper 42, but also includes a gas-barrier member 43 of a laminated metallic or resin film bonded to the top of shield 41 and extending over the entrance to a well 44 in stopper 42. Gas-barrier member 43 provides a cover for well 44 to prevent contamination that could be caused by the finger of a user entering well 44 and improves the vacuum retention of the tube assembly. Stopper 42 also includes an annular groove 45 through its top surface located between well 44 and the outer circumference of stopper 42. An undercut 46 is located at the bottom of groove 45 for receiving a cleat 48 at the end of each of a plurality of flexible fingers 47 that extend from the top of shield 41 into groove 45. Interaction between cleats 48 and undercut 46 in groove 45 retain stopper 42 within shield 41 without causing undesirable compression forces being applied to stopper 42 that would increase needle penetration force or detrimentally affect the pull out force required to remove closure 4 from the tube. Stopper 42 also includes a plug portion 49 having a convex bottom portion 49a extending from flange 44a. When closure 4 is on the open end of the tube, plug 49 is received in the open end to provide a vacuum tight seal with an inner wall of the tube. Where plug 49 contacts flange 44a, stopper 42 includes a channel 49b that receives and locks with a rim (not shown) around the open end of the tube.

Figure 5:
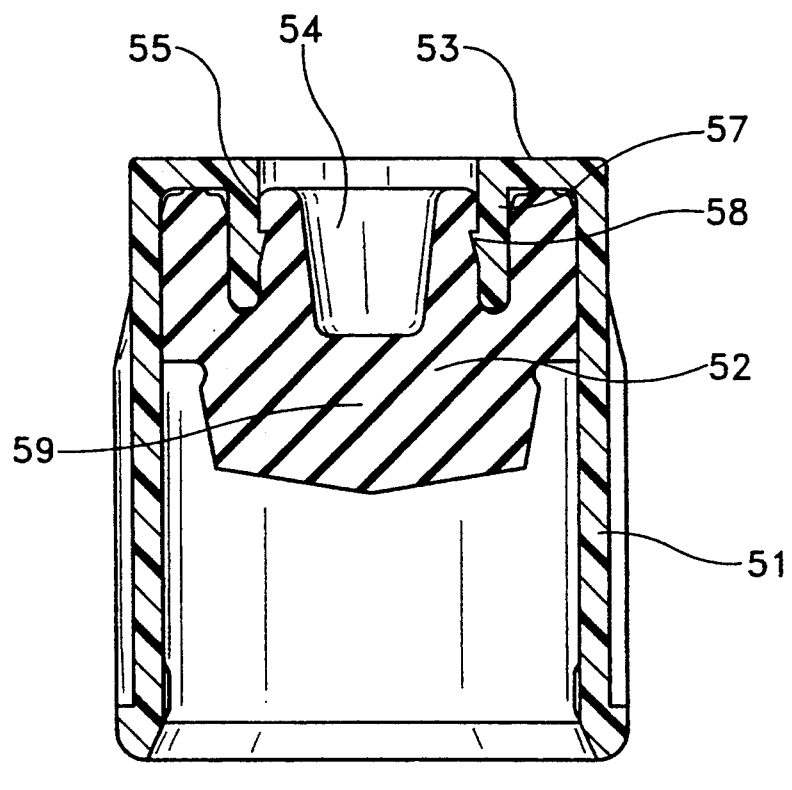

FIG. 5 is a cross-sectional view of a closure 5 that is substantially similar to closure 4 in FIG. 4, having a shield 51 and a stopper 52. Stopper 52 includes an annular groove 55 similar to groove 45 in closure 4. Shield 51, however, includes a spur 58 on the inside surface of each of a plurality of flexible fingers 57 to retain stopper 52 within shield 51. Each spur 5 8 embeds in the wall of groove 55 to prevent stopper 52 from separating from shield 51. Closure 5 also includes a gas barrier member 53 that is bonded to the top of shield 51 to prevent contamination of a well 54 and to improve the vacuum retention of the tube assembly and has a plug 59 that extends into the open end of the tube to provide a vacuum tight seal. The other features of closure 5 shown in FIG. 5 are similar to the features in closure 4.

Figure 6:
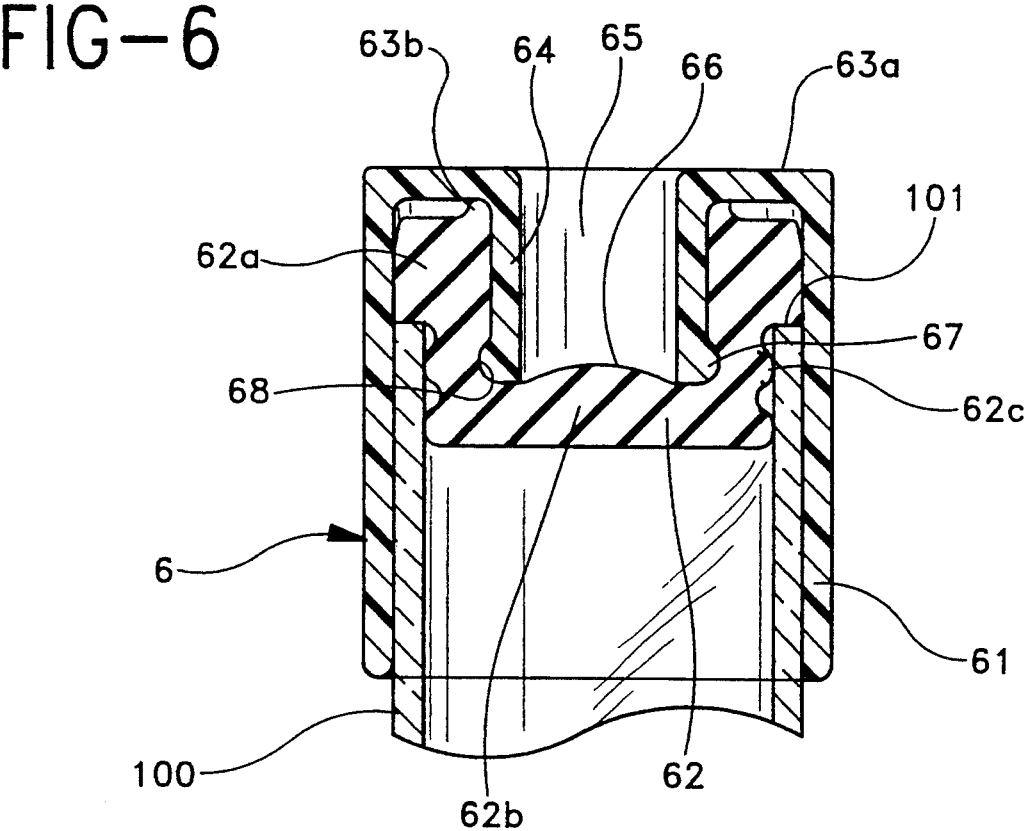

FIG. 6 is a cross-sectional view of an alternative embodiment of a closure 6 sealing a tube 100 according to the present invention that is similar to closure 1 shown in FIGS. 1 through 3, having a shield 61 for receiving a stopper 62. Closure 6 includes a gas-barrier member 63a of a laminated metallic or resin film bonded to the top of shield 61 and extending over the entrance to a well 65 in closure 6 to cover and prevent contamination of well 65. Closure 6 also includes a convex portion 66 at the base of well 65 that diverts residue body fluid left from a needle being withdrawn from stopper 62 away from the center and towards an outer wall of well 65. This feature is important since it prevents body fluid from collecting where the needle penetrated stopper 62, which minimizes the possibility of contaminating instrument probes used to draw a body fluid test sample out of tube 100 through stopper 62.

Shield 61 includes a plurality of flexible fingers 64 extending from the top of shield 61 and into well 65, with each flexible finger 64 having a cleat 67 extending from its proximal end into an undercut 68 at the base of well 65. As discussed above, the interaction between cleat 67 and undercut 68 retains the stopper within the shield to prevent them from being separated during use and minimizes the compression forces on stopper 62. Stopper 62 also includes a flange 62a that extends over an edge 101 of tube 100 to provide a secondary seal in combination with the primary seal provided by a plurality of sealing rings 62c surrounding the circumference of a plug portion 62b. Closure 6 also includes a sealing ring 63b located between stopper 62 and shield 61 and surrounding fingers 64 to prevent body fluid from flowing out of well 65 into the space between shield 61 and stopper 62 and provide additional sealing.

Figure 7:
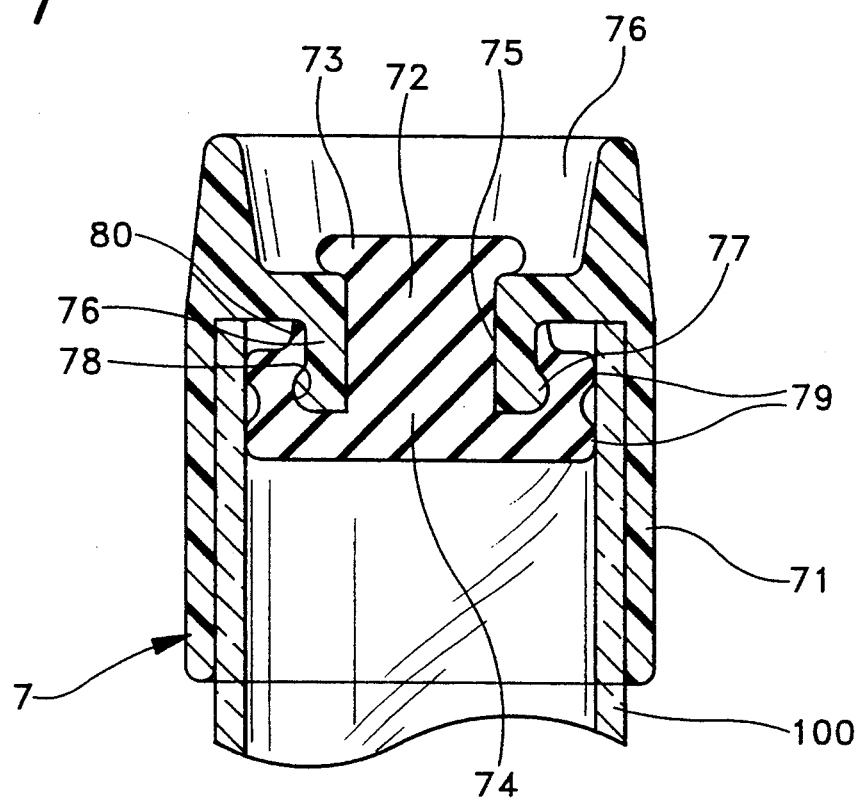

FIG. 7 is a cross-sectional view of a closure 7 on tube 100 having a shield 71 for receiving a stopper 72, wherein stopper 72 includes an upper flange portion 73 and a lower flange portion 74 that are positioned on opposite sides of a central aperture 75 formed from a plurality of flexible fingers 76 extending into shield 71 to securely hold stopper 72 within shield 71. The plurality of flexible fingers 76 surround the periphery of aperture 75 and each include a cleat 77 extending from its proximal end into an undercut 78 in stopper 72 to provide improved retention forces to hold stopper 72 within shield 71. Shield 71 also has an enlarged well portion 76 that is deep enough to prevent a user from contacting upper flange portion 73 and stopper 72 includes a plurality of sealing tings 79 around the circumference of lower flange portion 74 to seal the internal diameter at the open end of tube 100. Closure 7 also includes a sealing ring 80 between shield 71 and stopper 72 to prevent body fluid from flowing into undercut 78 and through aperture 75.

All of the above-described closures are manufactured using a molding process, wherein the shield is made of a harder plastic than the material used to make the stopper. Each stopper is made of a soft plastic or rubber to properly seal the open end of the tube, retain the vacuum within the tube, and be pierced by a needle. However, of course, these manufacturing techniques and materials are merely exemplary, various other manufacturing methods and materials could also be used.

In the foregoing discussion, it is to be understood that the above-described embodiments of the present invention are simply illustrative of various features that can be used in closures to be used to seal evacuated body fluid collection tubes. Other suitable variations, modifications and combinations of these features could be made to or used in these embodiments and still remain within the scope of the present invention.

What is claimed is:

1. A closure for sealing an open end of a body fluid collection tube comprising:
   a shield having a longitudinal axis and a plurality of flexible fingers extending from a top surface to a distal end within said shield, each of said plurality of flexible fingers having a cleat at said distal end extending away from said longitudinal axis; and
   a headless stopper for sealing a body fluid collection tube, said headless stopper including a well in a top surface having an undercut located around the bottom of said well that receives and mates with each cleat on said plurality of flexible fingers to securely retain said stopper within said shield.

2. A closure according to claim 1, wherein said shield further comprises a plurality of ribs on an outer surface of said shield to provide means for gripping said closure when being removed from the tube.

3. A closure according to claim 1, wherein said base of said well comprises a convex bottom surface that directs residue body fluid from said convex surface towards said undercut in said well.

4. A closure according to claim 1, wherein said shield further comprises an outer skirt having a plurality of protrusions extending from an interior surface of said outer skirt into said shield, wherein each of said plurality of protrusions are positioned to mate with a collar or ring on an outer wall of the tube to securely lock said closure onto the tube and retain a vacuum within the tube.

5. A closure according to claim 1, further comprising a gas-barrier member bonded to said shield to improve vacuum retention within the tube and protect said well from contamination.

6. A closure according to claim 1, wherein said stopper further comprises a plug having a plurality of sealing rings that form a primary seal with an inside wall at the open end of the tube.

7. A closure according to claim 6, wherein said plug includes a concave bottom surface to minimize the thickness of said stopper and minimize needle penetration force.

8. A closure according to claim 1, wherein said shield further comprises:
   a plurality of spokes extending radially from an opening in the top surface of said shield to support each of said plurality of flexible fingers; and
   a sealing ring between said shield and said stopper around said opening in the top surface of said shield to prevent body fluid from migrating out of said opening.

* * * * *